United States Patent [19]

Schwartz et al.

[11] Patent Number: 4,589,873

[45] Date of Patent: May 20, 1986

[54] METHOD OF APPLYING A HYDROPHILIC COATING TO A POLYMERIC SUBSTRATE AND ARTICLES PREPARED THEREBY

[75] Inventors: Abraham Schwartz; Jane Graper, both of Durham; Joel Williams, Cary, all of N.C.

[73] Assignee: Becton, Dickinson and Company, Paramus, N.J.

[21] Appl. No.: 614,620

[22] Filed: May 29, 1984

[51] Int. Cl.$^4$ .................... A61M 25/00; A41D 19/00
[52] U.S. Cl. ........................... 604/265; 2/167; 2/168; 427/2; 427/230; 427/307; 427/353; 427/393.5; 428/36; 428/411.1; 428/423.1; 428/451
[58] Field of Search .................. 427/2, 230, 307, 353, 427/393.5; 428/36, 411.1, 413.1, 451; 604/516–522, 264, 266; 138/145; 2/167, 168

[56] References Cited

U.S. PATENT DOCUMENTS

| | | | |
|---|---|---|---|
| 3,216,983 | 11/1965 | Shelanski et al. | 260/88.3 |
| 3,695,921 | 10/1972 | Shepherd et al. | 427/2 |
| 3,939,049 | 2/1976 | Ratner et al. | 204/159.13 |
| 4,055,682 | 10/1977 | Merrill | 427/2 |
| 4,087,567 | 5/1978 | Sullivan | 427/230 |
| 4,100,309 | 7/1978 | Micklus et al. | 427/2 |
| 4,112,925 | 9/1978 | Sullivan | 128/760 |
| 4,119,094 | 10/1978 | Micklus et al. | 126/132 R |
| 4,143,423 | 3/1979 | Sternlieb | 427/2 |
| 4,169,163 | 9/1979 | Judd et al. | 426/413 |
| 4,373,009 | 2/1983 | Winn | 428/424.2 |
| 4,381,008 | 4/1983 | Thomas et al. | 604/265 |
| 4,459,317 | 7/1984 | Lambert | 427/2 |
| 4,482,577 | 11/1984 | Goldstein et al. | 427/2 |

FOREIGN PATENT DOCUMENTS 1796134 2/1978 Fed. Rep. of Germany ... 427/393.5

*Primary Examiner*—John F. Niebling
*Assistant Examiner*—Terryence Chapman
*Attorney, Agent, or Firm*—Richard E. Brown

[57] ABSTRACT

A method to impart increased lubricity to the surface of a polymeric substrate includes contacting the substrate with a solution of a hydrophilic polymer in a solvent and heating the substrate to evaporate the solvent. The substrate retains a coating of the hydrophilic polymer, which, when dry, has about the same lubricity as the uncoated substrate. When wet, the coating becomes significantly more lubricious than when dry. The invention includes articles which have a lubricious surface when wet prepared by the method of the invention.

13 Claims, No Drawings

METHOD OF APPLYING A HYDROPHILIC COATING TO A POLYMERIC SUBSTRATE AND ARTICLES PREPARED THEREBY

BACKGROUND OF THE INVENTION

1. Field of the Invention

The present invention relates to a method for coating a polymeric substrate, and more particularly, relates to a method for applying a hydrophilic coating to a polymeric substrate to provide a lubricious surface to the substrate, and to articles having a lubricious surface prepared thereby.

2. Description of the Prior Art

Materials intended for fabrication of biomedical articles such as heart valves, catheters, intrauterine devices, wound drains and the like require a high degree of compatibility with body fluids and tissues. Some compatibility is afforded by hydrogels. These gels are polymeric in nature and swell with water to provide hydrophilic surfaces which have found wide application for various biomedical devices, particularly contact lenses. For some applications, however, it would be highly desirable to provide a surface having, in addition to hydrophilicity, a low coefficient of friction when in contact with an aqueous-based fluid, such as a body fluid. Such a low-friction surface would aid insertion or removal of a device into or out of a patient, and would contribute to patient comfort. Further, for ease of handling by a technician, it would be desirable if the surface retained a normal feel when dry and demonstrated its low-friction properties only when in contact with the aqueous-based medium.

Several methods have been used for attainment of low-friction surfaces on polymeric substrates. U.S. Pat. No. 4,381,008 to Thomas et al. discloses increased lubricity resulting from application of extrusion or stretching procedures to polymeric substrates. Coatings of various materials, such as silicone, fluorocarbon, or cellulose have been applied to polymeric substrates to decrease surface friction. Exemplary of such methods is that disclosed in U.S. Pat. No. 4,169,163 to Judd et al.

Polyvinyl pyrrolidone (PVP) is a water soluble hygroscopic polymer having excellent compatibility with body tissues. It is often copolymerized with another material to modify the PVP properties. U.S. Pat. No. 3,216,983 to Shelanski et al. discloses copolymers of PVP and various polyisocyanates which retain many of the desirable properties of PVP while reducing the water solubility and increasing adhesion of the copolymer to wood, glass, metal and the like. U.S. Pat. No. 3,939,049 to Ratner et al. discloses the grafting of PVP to polymer substrates after prior activation of the substrate surface by ionizing radiation. There is no teaching in the Ratner disclosure of surface lubricity.

U.S. Pat. No. 4,119,094 to Micklus et al. discloses a method to place a polyurethane - PVP interpolymer on a polymeric substrate and thereby provide a low friction surface to that substrate. The method of the Micklus et al. patent requires initial application of a polyisocyanate to the substrate, and the substrate must be one to which conventional polyurethanes adhere.

U.S. Pat. No. 4,373,009 to Winn discloses a modification of the Micklus et al. procedure in which the substrate is coated with a hydrophilic copolymer of PVP and a polymer containing active hydrogens. The substrate may be any material to which cured isocyanates adhere. The active hydrogens react with the polyisocyanate to form covalent bonds which are said to provide a more durable coating on the substrate than obtained by previous methods.

The surfaces prepared in accordance with the prior art methods described above do provide surface lubricity to the articles or substrates described, but all of these prior art methods still have disadvantages. In some, the surfaces are insufficiently lubricious for use as biomedical articles. Others require additional steps to introduce the desired surface lubricity, such as activation of the surface by radiation or use of an intermediate polyisocyanate bonding material between the substrate and the coating. Such additional steps increase the complexity and cost of manufacturing operations. Further, a PVP coating bonded to a polymeric substrate with a polyisocyanate, when in contact with water, comes off the substrate surface in flakes so that the aqueous medium becomes cloudy. Thus, there remains a distinct need for a better method to provide polymeric substrates with lubricious surfaces.

SUMMARY OF THE INVENTION

The present invention comprises a method for applying a coating of a hydrophilic polymer directly to a polymeric substrate whereby the surface of the coated substrate becomes lubricious when the surface is contacted with a liquid. The hydrophilic polymer is applied to the substrate by contacting the substrate with a solution of the hydrophilic polymer in a suitable applying solvent and removing the solvent by evaporation until the surface is no longer sticky.

In a preferred embodiment of this aspect of the invention, the hydrophilic polymer is PVP, the applying solvent is dimethylformamide (DMF), and the DMF is evaporated in a stream of hot air. The coated substrate may then be washed with a washing solvent to remove excess PVP and any residual DMF and dried to provide a surface which has substantially the same coefficient of friction as the uncoated substrate until contacted with an aqueous-based medium, whereupon the surface becomes lubricious.

The present invention includes articles having a lubricious surface provided by a coating of a hydrophilic polymer applied directly to the surface of the article by the method of the invention. Articles which are advantageously coated to provide a lubricious surface when wet may be prepared from tubing or sheeting made of most polymeric materials. Preferred embodiments of the invention are venous, urinary, and nasal catheters and examination gloves fabricated of polyvinyl chloride (PVC) and coated with PVP in accordance with the above-described method of the invention.

The method of the invention and articles prepared thereby overcome disadvantages associated with the prior art. The surfaces provided by the method of the invention are sufficiently lubricious to be used in substantially all biomedical applications without the need for additional lubricants. Because the articles made in accordance with the method of the invention do not become lubricious until they are contacted with an aqueous-based liquid, they can be handled with ease by an attendant and activated (i.e., rendered lubricious) at the moment of use. Further, only that portion of the article where lubricity is required need be activated. For example, only one or two fingers of examination gloves which may be used for rectal or pelvic examinations and the like need be activated. Normally colorless articles treated in accordance with the method of the invention remain colorless after prolonged periods of immersion in aqueous-based solutions, and the solutions themselves remain clear and colorless. In contrast, prior art methods based on isocyanate bonding layers such as taught by the previously mentioned patents of Micklus et al. and Winn, often lead, after prolonged immersion, to yellowed articles and milky solutions or flaking-off of the hydrophilic layer. Further, in accordance with the method of the present invention, the hydrophilic polymer bonds to the substrate directly with no requirement for a prior preparation step, such as radiation treatment, as taught by Ratner, or an intermediate layer of bonding material, such as polyurethane or polyisocyanate, as taught by Micklus et al. and Winn. This feature of the instant invention provides a substantial improvement over the art by reducing the cost of manufacture.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

According to the method of this invention, a polymeric substrate is coated with a hydrophilic polymer to provide the substrate with a surface which becomes lubricious when contacted with an aqueous-based liqiuid. Any polymeric substrate may be used, as, for example, a polyolefin, preferably, a vinyl polymer; however, other substrates may be used, as, for example, polyethylene, polypropylene, polyurethane, polytetrafluoroethylene, silicone, latex rubber and the like. Also within the scope of the invention are metal or ceramic materials with polymeric coatings. The substrate or article to be coated may be formed of any desired shape, size or configuration, such as valves, pins, sleeves, prosthetic devices, catheters, gloves, condoms and the like before the application of the coating. Alternatively, the coating may be applied when the substrate is in the form of sheeting or tubing and the like, and the desired articles shaped after the coating.

A suitable polymeric substrate for illustrating various features of the present invention is a PVC tubing. This tubing is contacted with a solution of a hydrophilic polymer in a suitable applying solvent. Although the preferred hydrophilic polymer is PVP and the invention will be illustrated using PVP, it is understood that other hydrophilic polymers, as, for example, polyethylene oxide, polyhydroxyethyl methacrylate, copolymers of PVP with vinyl sulfonic acid or other vinyl acids, or a mixture of hydrophilic polymers may be used. The molecular weight of the PVP may be from about 10,000 to 1,000,000, preferably from about 200,000 to 400,000.

Any applying solvent in which the hydrophilic polymer is soluble may be used for purposes of the present invention, and different applying solvents are preferred for application of coatings of the hydrophilic polymer to different polymeric substrates. If desired, a mixture of applying solvents may be used. The preferred applying solvent for coating a PVC tubing with PVP is DMF. Other suitable applying solvents are tetrahydrofuran (THF) ethyl lactate, butanone and dimethylacetamide. The concentration of PVP in the applying solvent is not critical. The preferred concentration, however, is from 0.1 to 10 percent, most preferably 4–5%. All concentrations, unless otherwise stated, are by volume.

Any suitable method, such as dipping, spraying or other practicable technique, may be used to contact the PVC tubing with the solution of PVP. Contact may be maintained for any appropriate length of time, preferably for from about 1 to 100 seconds, or longer, if necessary. The contact temperature is not critical. Preferably, contact is carried out at ambient temperature, but any temperature up to the boiling point of the applying solvent may be used. It is, however, understood that the preferred duration and temperature of contact may vary for other combinations of substrate and hydrophilic polymer.

When the step of contacting the PVC tubing with the solution of PVP is complete, the tubing is subjected to a drying step whereby the applying solvent is removed from the surface of the tubing. Any convenient method may be used for this drying step. Preferably, the tubing is heated to a suitable temperature from ambient to about 300° C. Most preferably, a temperature of from 150° C. to 250° C. is used. If desired, the rate of drying may be augmented by application of a partial vacuum or by the use of an air stream as, for example, from a heat gun.

The coated tubing, if desired, may be washed briefly in a washing solvent to remove any remaining applying solvent or any PVP which is not attached to the surface of the tubing as described below. Preferably, a washing solvent having a boiling point below about 100° C. is used for this purpose. Most preferably, water is used, although any other suitable washing solvent such as methanol, ethanol, acetone, THF, or acetronitrile may be used. The washing solvent is then removed by evaporation.

In an alternate embodiment of the invention, the polymeric substrate is immersed in an immersing solvent before being contacted with the PVP solution whereby the substrate surface is swelled by the immersing solvent, thereby permitting entry of more PVP into the polymeric surface. It is preferred that the immersing solvent be miscible with the solution of PVP in the applying solvent. Preferred immersing solvents are aromatic hydrocarbons such as benzene, toluene, xylene and the like; however, it is understood that any immersing solvent may be used which is capable of swelling a polymeric substrate. The duration and temperature of the immersion are not critical, and the immersion is preferably carried out at ambient temperature for from about 5 minutes to about 2 hours. Preferably, the substrate is transferred directly from the immersing solvent to the PVP solution without drying.

The coefficients of friction of the coated polymeric substrates of this invention may be determined as a measure of lubricity, and may be compared, both dry and wet, with the coefficients of friction of the corresponding uncoated substrates. Test D-1894-63 of the American Society for Testing and Materials (ASTM), 1973 Annual Book of ASTM Standards, Part 27, Plastics, p. 559 may be used to measure the coefficients of friction of flat coated surfaces of the presetn invention. The apparatus employed in the D-1894-63 test may be modified to allow testing of the coated polymeric tubing of the invention without any distortion or alteration, such as cutting the tubing open and laying it flat. Specifically, metal rods are inserted into two pieces of tubing to be tested, and the rods are placed in a pair of grooves milled into the standard sled of the D-1894-63 apparatus. The procedure set forth in the D-1894-63 test is then exactly followed.

Polymeric substrates coated according to the method of this invention have, when dry, about the same coefficient of friction as the uncoated substrates. When wet, the coated substrates have coefficients of friction from about 0.05 to 0.5 depending on the nature of the substrate, the hydrophilic polymer used for the coating, and the conditions of time, temperature, solvent and the like used during the coating process. When PVC tubing is coated with PVP in accordance with the preferred conditions of the present invention, the observed coefficient of friction is generally from about 0.1 to about 0.3 and represents an improvement in lubricity of up to 700% in comparison to uncoated tubing.

It is believed, although as yet unsubstantiated, that the polymeric substrate surfaces coated by the method of this invention are swelled by contact with the applying solvent so that portions, most likely ends, of the PVP molecules enter into the polymeric surface. When the applying solvent is removed during the evaporation step, the substrate surface apparently shrinks back to normal, and portions of the PVP chains are thereby trapped in the substrate surface and substantially stabilized against removal. It is further postulated that lubricity is achieved by the method of the present invention by a very slow separation of the PVP molecules from the substrate surface.

EXAMPLE 1

Four grams of PVP (MW 360,000) were dissolved in 100 ml of DMF. PVC tubing (3.35mm inside diameter and 4.65mm outside diameter) was plugged at one end, and the plugged end dipped into the PVP-DMF solution for 5 seconds at room temperature. The tubing was dried by a hot air gun at 200° C. for 1 minute until the coating was completely dry and no longer sticky. When tested by the modified apparatus used in the D-1894-63 test, as described above, the coated and uncoated tubing, when dry, both had a coefficient of friction of 0.6 against a test surface of vinyl sheeting. After immersion under water for several seconds, the coefficient of friction of the coated tubing was 0.1. The coefficient of friction of the uncoated tubing did not significantly change when wet.

EXAMPLE 2

Five grams of PVP (MW 360,000) was dissolved in a mixture of 50 ml each of DMF and methanol. Thin (0.127mm) PVC examination gloves were dipped into this solution for about 1 second at room temperature, then removed and dried for 1 hour at room temperature. When tested by the method of test D-1894-63, the gloves had, when dry, the same coefficient of friction before and after coating. When wet, the coated gloves became sufficiently lubricious to be used for rectal or pelvic examination without additional lubricant.

EXAMPLE 3

The procedure of Example 1 was repeated except the PVP coating was applied to polyurethane venous and urinary catheters. The coated and uncoated catheters both had a coefficient of friction of 0.5 against a test surface of vinyl sheeting when dry. The coated catheters had a coefficient of friction of 0.1 against vinyl sheeting when wet. The coefficient of friction of the uncoated catheters was the same when wet as when dry.

EXAMPLE 4

The procedure of Example 1 was used to apply a PVP coating to latex rubber gloves and condoms except that a 5% PVP solution of ethyl lactate was used. The surfaces of the coated gloves and condoms were sufficiently lubricious to be useful without additional lubricants.

EXAMPLE 5

Silicone rubber tubes were immersed in xylene for 30 minutes at room temperature, then subjected to the procedure of Example 1 to provide the tubes with a lubricious surface. The tubes may be used as feeding tubes wherein the lubricious surfaces provide ease of nasal insertion and removal.

Thus, the method of the present invention provides a polymeric substrate with a coating of a hydrophilic polymer, preferably PVP, which has essentially the same coefficient of friction as the uncoated substrate when dry, but which becomes substantially more lubricious when wet. The coating is applied by contacting the polymeric substrate with a solution of a hydrophilic polymer in a solvent, and then evaporating the solvent. The coated surface may optionally be washed with a low boiling solvent to remove the contacting solvent and any excess PVP. The resulting hydrophilic and lubricious coating does not flake off when exposed to water for extended periods as do coatings of PVP bonded to polymeric surfaces with polyisocyanates. When immersed in water for extended periods, the water remains clear and colorless, and the coating itself does not develop a yellow cast.

What is claimed is:

1. A method of coating a polymeric substrate comprising contacting a polymeric substrate with a solution of polyvinyl pyrrolidone in an applying solvent selected from the group of solvents consisting of dimethyl formamide, butanone, methanol, tetrahydrofuran and dimethyl acetamide and evaporating said solvent from said substrate so that the surface of said substrate retains a coating of said polyvinyl pyrrolidone to thereby provide the surface of said coated substrate with lubricity when said coated substrate is contacted with an aqueous-based liquid.

2. The method in accordance with claim 1 wherein said substrate is a polymer selected from the group consisting of polyvinyl chloride, polyethylene, polypropylene, polytetrafluoroethylene, polyurethane, latex rubber.

3. The method in accordance with claim 1 wherein said applying solvent is a mixture of solvents.

4. The method in accordance with claim 1 further comprising washing said substrate with a washing solvent after said evaporating to remove excess polyvinyl pyrrolidone from the surface of said coated substrate and drying said coated substrate to remove said washing solvent from the surface of said coated substrate.

5. The method in accordance with claim 4 wherein said washing solvent is selected from group of solvents consisting of water, acetone, acetontrile, methanol, ethanol, isopropanol and tetrahydrofuran.

6. The method in accordance with claim 1 further comprising immersing said polymeric substrate in an immersing solvent before said contacting wherein said substrate is swelled by said immersing solvent before said contacting.

7. A method of rendering the surface of a polymeric substrate more lubricious comprising contacting a polyvinyl chloride substrate having a first surface coefficient of friction with a solution of polyvinyl pyrrolidone in dimethyl formamide, heating said substrate to evaporate said dimethyl formamide whereby the surface of said polyvinyl chloride substrate retains a coating of said polyvinyl pyrrolidone, washing said coated substrate with water to remove excess polyvinyl pyrrolidone, and drying said coated substrate to remove said water from the surface of said coated substrate to provide the surface of said coated substrate with a second surface coefficient of friction lower than said first coefficient of friction to thereby render said coated substrate more lubricious when said coated substrate is contacted with an aqueous-based liquid.

8. A catheter having a lubricious surface when wet prepared by the method of claim 7.

9. An examination glove having a lubricious surface when wet prepared by the method of claim 7.

10. An article consisting of a polymeric substrate selected from the group of substrates consisting of polyvinyl chloride, polyethylene, polypropylene, polytetrafluoroethylene, polyurethane and latex rubber having a coating of polyvinyl pyrrolidone directly on said substrate whereby the surface of said substrate having said polyvinyl pyrrolidone coating and the surface of said substrate without said coating have substantially the same surface coefficient of friction when dry, but the surface of said substrate having said polyvinyl pyrrolidone coating when wet has a coefficient of friction which is lower than the coefficient of friction of said surface of said substrate without said coating when wet.

11. The article of claim 10 which is a polyvinyl chloride catheter and having a coefficient of friction when wet of about 0.1 to 0.3.

12. The article of claim 10 which is a polyvinyl chloride examination glove having a coefficient of friction of about 0.1 to 0.3.

13. A method of coating a polymeric substrate comprising immersing a polymeric substrate in an immersing solvent selected from the group of solvents consisting of benzene, toluene and xylene wherein said substrate is swelled, contacting said substrate with a solution of polyvinyl pyrrolidone in an applying solvent, and evaporating said applying solvent from said substrate so that the surface of said substrate retains a coating of said polyvinyl pyrrolidone to thereby provide the surface of said coated substrate with lubricity when said coated substrate is contacted with an aqueous-based liquid.

* * * * *